United States Patent
Franczyk, II et al.

(10) Patent No.: US 6,646,160 B2
(45) Date of Patent: Nov. 11, 2003

(54) PROCESS FOR THE PREPARATION OF CARBOXYLIC ACID SALTS FROM PRIMARY ALCOHOLS

(75) Inventors: Thaddeus S. Franczyk, II, Chesterfield, MO (US); William L. Moench, Jr., Town and Country, MO (US)

(73) Assignee: Monsanto Technology, LLC, St. Louis, MO (US)

( * ) Notice: Subject to any disclaimer, the term of this patent is extended or adjusted under 35 U.S.C. 154(b) by 0 days.

(21) Appl. No.: 09/563,683

(22) Filed: May 3, 2000

(65) Prior Publication Data

US 2003/0097020 A1 May 22, 2003

Related U.S. Application Data

(60) Provisional application No. 60/132,261, filed on May 3, 1999.

(51) Int. Cl.$^7$ .............................................. C07C 51/291
(52) U.S. Cl. ........................ 562/539; 562/538; 562/512
(58) Field of Search ................................ 562/538, 539, 562/512

(56) References Cited

U.S. PATENT DOCUMENTS

| | | | |
|---|---|---|---|
| 2,384,816 A | 9/1945 | Curme et al. ................ | 260/531 |
| 2,384,817 A | 9/1945 | Chitwood et al. .......... | 260/531 |
| 3,449,413 A | 6/1969 | Hartel et al. ................ | 260/523 |
| 3,620,991 A * | 11/1971 | Wasser ....................... | 260/29.6 |
| 3,997,478 A | 12/1976 | Petro ........................... | 252/470 |
| 4,321,285 A | 3/1982 | Feldstein .................... | 427/97 |
| 4,547,324 A | 10/1985 | Wong et al. .......... | 260/502.4 R |
| 4,782,183 A | 11/1988 | Goto et al. ................. | 562/526 |
| 4,810,426 A | 3/1989 | Fields, Jr. et al. ..... | 260/502.5 F |
| 4,847,013 A | 7/1989 | Müller ........................ | 562/17 |
| 5,068,404 A | 11/1991 | Miller et al. .................. | 502/17 |
| H1193 H | 6/1993 | Batra et al. .................... | 75/352 |
| 5,220,054 A | 6/1993 | Urano et al. .................. | 562/539 |
| 5,220,055 A | 6/1993 | Urano et al. ................. | 562/539 |
| 5,225,592 A | 7/1993 | Ochoa Gomez et al. .... | 562/526 |
| 5,292,936 A | 3/1994 | Franczyk ..................... | 562/526 |
| 5,367,112 A | 11/1994 | Franczyk ..................... | 562/526 |
| 5,397,477 A * | 3/1995 | Salem et al. ................. | 210/683 |
| 5,627,125 A | 5/1997 | Ebner et al. ................. | 502/331 |
| 5,689,000 A | 11/1997 | Ebner et al. ................. | 562/539 |
| 5,739,390 A * | 4/1998 | Franczyk et al. ........... | 562/526 |
| 6,239,312 B1 * | 5/2001 | Villanti et al. ............... | 562/526 |

FOREIGN PATENT DOCUMENTS

| | | | |
|---|---|---|---|
| EP | 0 297 369 A2 | 1/1989 | ............. C07F/9/38 |
| EP | 0 504 381 A1 | 9/1992 | ......... C07C/227/02 |
| EP | 0 945 428 A2 | 9/1999 | ......... C07C/227/02 |
| GB | 2 148 287 | 5/1985 | ........... C07C/99/00 |
| JP | 09-151168 * | 6/1997 | ......... C07C/229/08 |
| WO | WO 92/06069 | 10/1990 | ......... C07C/227/02 |

OTHER PUBLICATIONS

Laine et al. "Structure and Activity of Chromium–Promoted Raney Copper Catalysts for Carbon Monoxide Oxidation", *Applied Catalysis*, 44 (1988) pp. 11–22.

Anonymous "Improved Process for Producing Aminocarboxylic Acid Salt", No. 35437, *Research Disclosure* (Oct. 1993).

Derwent WPI Database, Accession No. 1997–359115 (Abstract of JP 09–151168, Jun. 10, 1997).

* cited by examiner

*Primary Examiner*—Paul J. Killos
(74) *Attorney, Agent, or Firm*—Ira D. Finkelstein; Howrey Simon Arnold & White, LLP

(57) ABSTRACT

The present invention provides a new and useful improvement in the process to manufacture a carboxylic acid salt, particularly an amino carboxylic acid salt, from a primary alcohol, particularly a primary aminoalcohol. The process of manufacturing amino carboxylic acid salts comprises contacting an aqueous solution of a primary aminoalcohol with a strong hydroxide base selected from the group consisting of an alkali metal hydroxide, an alkaline earth metal hydroxide, an ammonium hydroxide compound including a tetraalkyl ammonium hydroxide, or the like, in the presence of an effective amount of a catalyst. The catalyst comprises one or more of elements selected from the group consisting of copper, cobalt, nickel, and cadmium as well as optionally lesser amounts of chromium, titanium, niobium, tantalum, zirconium, vanadium, molybdenum, manganese, tungsten, cobalt, nickel, or mixtures thereof. The reaction mixture contains less than about 3000 ppm, preferably less than about 500 ppm, more preferably less than about 100 ppm of oxidized copper ($Cu^+$ and/or $Cu^{2+}$) during the reaction. The concentration of oxidizing agents in the reactants is minimized to prevent formation of oxidized copper from metallic copper catalyst.

39 Claims, No Drawings

PROCESS FOR THE PREPARATION OF CARBOXYLIC ACID SALTS FROM PRIMARY ALCOHOLS

This application claims the benefit of U.S. Provisional Application No. 60/132,261, filed May 3, 1999, the disclosure of which is incorporated herein by reference.

BACKGROUND OF THE INVENTION

1. Field of the Invention

This invention relates to the preparation of carboxylic acid salts, and more particularly, to a method for the preparation of amino carboxylic acid salts by the reaction of primary aminoalcohols with a hydroxide base in the presence of a catalyst.

2. Description of Related Art

Carboxylic acid salts are useful in various applications. The salts can be neutralized to the corresponding acid which is also useful in a number of applications, such as a raw material for pharmaceuticals, agricultural chemicals, pesticides and the like. Many of such carboxylic acids are available commercially in large quantities.

Copper catalysts are known to be effective for the conversion of primary alcohols to carboxylic acid salts (Chitwood 1945) and, particularly, alkanolamines to aminocarboxylic acids (Goto et al. 1988). The prior art maintains that both metallic copper and copper salts or oxides ($Cu^+$, $Cu^{2+}$, or both) are suitable catalysts to facilitate this conversion.

A journal article "Structure and Activity of Chromium-Promoted Raney Copper Catalyst for Carbon Monoxide Oxidation" by Laine et al., *Applied Catalysis*, 44 (1–2), pages 11–22, discloses that chromium-promoted Raney copper catalysts were prepared, and their activity for the oxidation of carbon monoxide was measured. The surface area of the Raney copper catalyst was directly related to the aluminum content in the precursor alloy and to a lesser extent to the presence of chromium. Bulk cuprous oxide and cupric oxide were detected by x-ray diffraction in the Raney copper catalyst. The presence of chromium inhibited the formation of cupric oxide but not of cuprous oxide. The activity decreased as chromium content increased.

U.S. Pat. No. 4,782,183 to Goto et al. describes a method for the manufacture of amino carboxylic acid salts which comprises contacting an aminoalcohol with an alkali metal hydroxide in the presence of a Raney copper catalyst, or a copper catalyst supported on zirconium oxide. The catalyst can also be an inorganic or organic salt of copper, or an oxidized surface of a metallic copper that is then reduced with hydrogen.

U.S. Pat. No. 4,810,426 to Fields et al. describes a process for the production of N-phosphonomethylglycine by oxidizing N-phosphonomethylethanolamine, or the cyclic internal ester thereof, with an excess of an aqueous alkali and a copper catalyst, and thereafter, heating at a temperature between 200° C. and 300° C. The catalyst is selected from cadmium, zinc, copper, palladium, platinum, and their respective oxides, hydroxides, and salts.

U.S. Pat. No. 5,220,054 to Urano et al. describes a method for the manufacture is of amino carboxylic acid by the oxidative dehydrogenation reaction in the presence of an alkali metal hydroxide, a copper containing catalyst, and water characterized by maintaining the nickel concentration below 40 ppm.

U.S. Pat. No. 5,292,936 to Franczyk describes an improved process to prepare an amino carboxylic acid salt. According to the process an aqueous solution of an aminoalcohol is contacted with an alkali metal hydroxide in the presence of an effective amount of a Raney copper catalyst that has from about 50 parts per million to about 10,000 parts per million of an element selected from the group consisting of chromium, titanium, niobium, tantalum, zirconium, vanadium, molybdenum, manganese, tungsten, cobalt, nickel and mixtures thereof.

Although satisfactory results are achieved by the processes of the prior art to convert an alcohol to a carboxylate using a copper catalyst, or even a Raney copper catalyst, it has now been found, in accordance with the teachings of the present invention, that the process of the present invention can convert an alcohol to an acid salt with greater conversion. This increase in yield and selectivity results in significant capital savings and operating costs when such reactions are practiced on a commercial scale.

SUMMARY OF THE INVENTION

The present invention provides a new and useful improvement in the process to manufacture a carboxylic acid salt, particularly an amino carboxylic acid salt, from a primary alcohol, particularly a primary aminoalcohol.

The process of manufacturing amino carboxylic acids salts comprises contacting an aqueous solution of a primary aminoalcohol with a strong hydroxide base selected from the group consisting of an alkali metal hydroxide, an alkaline earth metal hydroxide, an ammonium hydroxide compound including a tetraalkyl ammonium hydroxide, or the like, to form a reaction mixture, in the presence of an effective amount of a catalyst. The primary aminoalcohol and the strong hydroxide base react in the reaction mixture to form an amino carboxylic acid salt. The catalyst comprises one or more of elements selected is from the group consisting of copper, cobalt, nickel, and cadmium as well as optionally lesser amounts of chromium, titanium, niobium, tantalum, zirconium, vanadium, molybdenum, manganese, tungsten, cobalt, nickel, and mixtures thereof.

The reaction mixture contains less than about 3000 ppm, preferably less than about 500 ppm, more preferably less than about 100 ppm of oxidized copper either in soluble, complexed, colloidal, or particulate form during the reaction. The copper containing catalyst contains less than 50 ppm by weight, preferably less than 10 ppm by weight, more preferably less than 1 ppm by weight, of oxidized copper compared to the weight of active catalyst prior to starting the reaction. Examples of oxidized copper include cupric and cuprous ions, copper oxides, copper hydroxides, and the like. The presence of oxidized copper leads to poorer catalytic selectivity and activity.

The concentration of oxidizing agents in the reactants is minimized to prevent formation of oxidized copper from metallic copper catalyst. The concentration of oxidizing agents in the feedstocks and in the reaction mixture is preferably less than about 1000 ppm total, more preferably less than about 500 ppm total, even more preferably less than about 200 ppm total, and most preferably less than about 40 ppm.

DETAILED DESCRIPTION OF THE INVENTION

The present invention provides a new and useful improvement in the process to manufacture a carboxylic acid salt from a primary alcohol. More particularly, the present invention provides a new and useful improvement in the process to manufacture an amino carboxylic acid salt from a primary aminoalcohol.

The primary alcohols which are useful as starting materials in the process of the present invention can be monohydric or polyhydric, and also aliphatic, cyclic or aromatic compounds, including polyether glycols, which react with a strong base to form a carboxylate. It is necessary that the alcohol and the resulting carboxylate are stable in the strongly caustic mixture, and that the alcohol is somewhat water soluble.

Suitable primary monohydric alcohols include aliphatic alcohols which can be branched, straight-chain, or cyclic, and aromatic alcohols such as benzyl alcohol. The alcohols can be substituted with various non-hindering groups, provided that these substituent groups do not react with the hydroxide base or the catalyst at the temperatures and pressures for the conversion of the alcohol to the acid. Suitable aliphatic alcohols include ethanol, propanol, butanol, pentanol, and the like.

Aminoalcohols represented by the formula

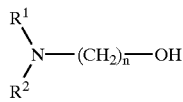

are also useful as starting materials in the present process where n is from 2 to about 20. When $R^1$ and $R^2$ are both hydrogen and n is 2, the aminoalcohol is monoethanolamine. When one of $R^1$ and $R^2$ is —$CH_2CH_2OH$ or —$CH_2COOH$, and the other R group is hydrogen and n is 2, the resulting product from the aminoalcohol is an iminodiacetate salt. When both $R^1$ and $R^2$ are —$CH_2CH_2OH$ or —$CH_2COOH$, the resulting product from the aminoalcohol is a nitrilotriacetate salt. Specific aminoalcohols include, for example, n-hydroxyethylglycine acid, monoethanolamine, diethanolamine, triethanolamine, N-methyethanolamine, N-ethylethanolamine, N-isopropylethanolamine, N-butylethanol-amine, N-nonylethanolamine, N-(2-aminoethyl) ethanolamine, N-(3-aminopropyl) ethanolamine, N,N-dimethylethanolamine, N,N-diethylethanolamine, N,N-dibutyl-ethanolamine, N-methyldiethanolamine, N-ethyldiethanolamine, N-propyldiethanol-amine, N-butyldiethanolamine, N-methyl-N-(3-aminopropyl) ethanolamine, 3-amino-propanol, and salts thereof.

In the above formula, $R^1$ and/or $R^2$ can also be an alkyl group having from 1 to 6 carbon atoms, for example, methyl, ethyl, propyl, isopropyl, butyl, isobutyl and the like. There would then be provided corresponding amino acids with these alkyl groups which would be useful in a number of applications. $R^1$ or $R^2$ can also be a phosphonomethyl group such that the starting amino acid would be N-phosphonomethylethanolamine, and the resulting amino acid salt would be the salt of N-phosphonomethylglycine. If one of $R^1$ or $R^2$ were phosphonomethyl, and the other were —$CH_2CH_2OH$, the resulting amino acid salt would be the salt of N-phosphonomethyliminodiacetic acid, which can be converted to N-phosphonomethylglycine by any number of techniques known to those skilled in the art. If one of $R^1$ or $R^2$ were phosphonomethyl, and the other were a lower alkyl group, the resulting amino acid salt would be an N-alkyl-N-phosphonomethylglycinate which could be converted to N-phosphonomethylglycine by the teachings in U.S. Pat. No. 5,068,404 to Miller and Balthazor, which is incorporated by reference herein.

A commercially important embodiment is where the aminoalcohol is diethanolamine, the strong hydroxide base is sodium hydroxide, the catalyst is comprised of Raney copper or metallic copper on an inert support, and the amino carboxylic acid salt product is disodium iminodiacetate.

Manufacturing carboxylic acids salts comprises contacting an aqueous solution of a primary alcohol with a strong hydroxide base. The hydroxide base suitable for use in the process of the present invention include the alkaline earth metal hydroxide, such as magnesium hydroxide, calcium hydroxide, barium hydroxide and the like. The hydroxide base can also be a tetraalkyl ammonium hydroxide having up to 5 carbon atoms in each alkyl group, such as tetramethyl ammonium hydroxide, dimethyldipropyl ammonium hydroxide, tributylethyl ammonium hydroxide and the like. The hydroxide base may be other ammonium compounds. However, alkali metal hydroxides are preferred. Suitable alkali metal hydroxides for use in the process of the present invention include lithium hydroxide, sodium hydroxide, potassium hydroxide, rubidium hydroxide and cesium hydroxide. Because of their ready availability and ease of handling, sodium hydroxide and potassium hydroxide are preferred, and sodium hydroxide is especially preferred. The amount of the hydroxide base to be used is an equivalent amount in the range of about 1 to about 2 equivalents relative to the hydroxyl group of the alcohol to be used in the reaction. The hydroxide can be in any convenient form, for example flakes, powder, pellets or an aqueous solution.

Manufacturing carboxylic acids salts comprises contacting an aqueous solution of a primary alcohol with a strong hydroxide base in the presence of an effective amount of a catalyst.

The preferred catalyst contains metallic copper. One catalyst useful in this invention consists essentially of a hydroxide-resistant support; an anchor metal selected from the group consisting of platinum, palladium, ruthenium, silver, gold, and mixtures thereof deposited on the support; and an element selected from the group consisting of copper, cobalt, nickel, cadmium, and mixtures thereof on or combined with the anchor metal. The catalyst may contain other heavy metals as described in U.S. Pat. No. 5,292,936, whose disclosure is incorporated herein by reference. These other heavy metals include chromium, titanium, niobium, tantalum, zirconium, vanadium, molybdenum, manganese, tungsten, cobalt, nickel and mixtures thereof.

The catalyst composition may be any catalyst known or developed by one in the art provided the limits on oxidized copper are met. The method of making the catalyst may be any method known to the art, for example, by electroless metal deposition as described in U.S. Pat. No. 5,627,125, or by the process described in U.S. Pat. No. 5,689,000, the disclosures of which are incorporated herein by reference. Electroless metal deposition refers to the chemical deposition of an adherent metal coating on a suitable substrate in the absence of an external electric source. The anchor metal deposited on the hydroxide-resistant support can be a noble metal, for example silver, gold, platinum, palladium or ruthenium or mixtures thereof. Platinum is preferred. A mixture may include an alloy comprising at least two noble metals, or may include two or more noble metals added sequentially to the hydroxide-resistant support.

The hydroxide-resistant support in the catalyst is necessary since the reaction to convert the alcohol to the corresponding acid salt is conducted in a strong basic solution. Suitable supports include titanium oxide, zirconium oxide and carbon. Carbon is preferred. Suitable hydroxide-resistant supports containing a suitable anchor metal can be obtained commercially.

Alternatively, another catalyst useful for the present invention is a Raney copper catalyst that may contain lesser amounts of chromium, titanium, niobium, tantalum, zirconium, vanadium, molybdenum, manganese, tungsten, cobalt, nickel and mixtures thereof.

The amount of catalyst to be used to convert the alcohol to the corresponding acid can range between about 1% and about 70% by weight, preferably 1 to 40% by weight, based on the amount of the starting alcohol.

The presence of oxidized copper leads to poorer catalytic selectivity and activity. This finding was unexpected based upon the prior art that purports that excellent yields of amino acids can be obtained when oxidants such as oxygen are introduced into the reaction mixture.

It is advantageous to maintain the amount of oxidized copper ($Cu^+$ and/or $Cu^{2+}$) in the reaction mixture to below about 3000 ppm, preferably below about 500 ppm, more preferably below about 100 ppm, and most preferably below about 50 ppm.

The term "oxidized copper" includes cupric and cuprous ions, copper oxides, copper hydroxides, or other copper salts, wherein the oxidized copper is exposed or available to the fluids, and wherein the oxidized copper is in the form of either particulate, colloidal, complexed, or soluble form.

The term "particulate form" includes oxidized copper attached to or embedded in, the catalyst, so long as the oxidized can contact fluid.

The term "reaction mixture" is defined as the totality of material that takes part in the reaction, i.e., the alcohol, the base, the solvents, the catalyst that is exposed to the fluids, the gas charged to the reactor, and any other adjuvants.

It is also desirable to treat the copper containing catalyst to ensure that the catalyst has essentially no, i.e., less than 500 ppm by weight, preferably less than 100 ppm by weight, more preferably less than 40 ppm by weight, of oxidized copper compared to the weight of catalyst prior to starting the reaction.

As used herein the term "catalyst" includes the material exposed to the fluids, but not any inert material or material not exposed to fluids. For example, a completely reduced copper plating completely surrounding a particle of copper oxide, so that the copper oxide is not exposed to the fluid, would contain for purposes of this disclosure no oxidized copper.

The reaction mixture contains less than about 3000 ppm, preferably less than about 1000 ppm, of oxidized copper either in soluble, complexed, colloidal, or particulate form both before and during the reaction. It is more preferred that the reaction mixture contains less than about 100 ppm, and most preferably less than about 50 ppm, of oxidized copper either in soluble, complexed, colloidal, or particulate form before and during the reaction.

The amount of oxidized copper may increase at the start of the reaction, as oxidizing agents present in the reaction mixture contact and react with the catalyst. The reaction environment is highly reducing, however, and it is recognized by those skilled in the art that the concentration of oxidized copper in the reaction mixture will thereafter generally decline over time.

Oxidized copper can originate from, for example, poorly reduced or oxidized copper catalysts or by the introduction of oxidizing agents such as molecular oxygen, ozone, and salts of chlorates, chlorites, hypochlorites, and perchlorates. The presence of these oxidizing agents can oxidize some of the catalyst, forming cupric or cuprous ions.

The quantity of oxidized copper can be reduced in a number of ways. First, it may be possible to reduce the dissolved molecular oxygen concentration in the reaction mixture. The concentration of dissolved molecular oxygen in the mixture is advantageously less than about 5 ppm, more preferably less than about 1 ppm, and even more preferably less than about 0.5 ppm.

This can be done with sequestering agents or by other techniques known to the art. Preventing oxygen from contacting a copper catalyst is one method. This can be done by keeping the catalyst under a fluid, for example under water.

Simple exclusion of air from the reactor, and of de-aerating feedstocks, i.e., the primary alcohol and the strong hydroxide base, by vacuum or by inert gas purge, will reduce the amount of oxygen in the reaction mixture. Air can be removed from a reactor by displacement with fluids, by displacement with another gas, by vacuum, or by a combination thereof. Oxygen can be purged from the mixture, or from individual feedstocks, by bubbling through the mixture a gas containing little oxygen, such as nitrogen or hydrogen.

Oxygen scavengers can be added to the mixture, or to one or more feedstocks, to reduce dissolved oxygen. Examples of oxygen scavengers include sulfites such as sodium sulfite. An effective amount of an oxygen scavenger is generally between about 5 ppm to about 50 ppm.

Other oxygenating agents, such as chlorite, chlorate, perchlorate, and hypochlorite salts, can be excluded from the reaction mixture by a variety of methods. First, feedstocks may be selected that contain little of the above oxidizing agents. Commercial hydroxide solutions can contain between 100 and 5000 ppm oxidizing agents. One mole of sodium chlorate, for example, can theoretically generate three to six moles of oxidized copper from the catalyst. Sodium hydroxide, the lowest-cost alkali hydroxide used for the conversion of aminoalcohols to aminocarboxylic acid salts, is often commercially produced by electrolysis of NaCl solutions. This process co-produces varying amounts of chlorine oxides, chiefly in the form of sodium chlorate ($NaClO_3$). Use of sodium hydroxide containing sodium chlorate results in poorer selectivity in the conversion of aminoalcohols.

While not being bound to any theory, it is believed these oxidizing agents oxidize the copper-containing catalyst. Said catalyst may well be reduced, or partially reduced, during the course of the reaction.

Quantities of oxidizing agents and of oxidized copper in feedstocks and in the reaction mixture can be eliminated by exposure to a reducing agent, for example, a metal hydride, sodium borohydride, formaldehyde, molecular hydrogen, hydrazine, formic acid or salt thereof. The concentration of these oxidizing agents in both the feedstocks and in the reaction mixture is preferably less than about 1000 ppm total, more preferably less than about 500 ppm total, even more preferably less than about 200 ppm total, and most preferably less than about 40 ppm. The amount of reducing agent added should be at least sufficient to reduce the concentration of oxidizing agents to below that level. An excess is preferred. The absolute amount of reducing agents will depend on the concentration of oxidizing agents in the feedstock.

It is preferred that the concentration of these oxidizing reagents be reduced prior to exposing the various feeds, including the primary alcohol and the strong hydroxide base, to the catalyst.

Oxidized copper ions may be removed from the system. An effective quantity of acid or chelating acid may typically be between about 500 ppm and about 5000 ppm. The oxidized copper or other metal ions also may be removed from the reaction mixture, or from the separate feedstocks, by known means, for example by exposing the reaction mixture or the feedstocks to ion exchange resins.

Finally, the presence of oxidized copper on the surface of the catalyst prior to introduction of the fluid feedstocks has been found to be a source of oxidized copper.

The copper ions on a catalyst may be removed by washing the catalyst with an acid, for example, an organic acid or an inorganic acid, or with a chelating acid, for example, EDTA. The washing may effectively remove the copper ions from the catalytic agent, and the washing fluid can be withdrawn before introduction. An effective quantity of acid or chelating acid may typically be between about 10 ppm and about 5000 ppm. Use of deaerated fluids for washing and rinsing, that may optionally contain oxygen scavengers, will help prevent formation of additional oxidized copper.

The catalyst may be pretreated with a reducing agent, for example, a metal hydride, sodium borohydride, formaldehyde, molecular hydrogen, hydrazine, formic acid or salt thereof. While these compounds may also be added to the feedstock, it may be desirable to treat the catalyst with these agents before introducing the liquid feeds. Said reducing agents may be contacted with the catalyst as a fluid, a vapor, or a gas. The expedient of charging the reactor with hydrogen gas will reduce oxidized copper on the catalyst.

In the process of the present invention, it is necessary to contact the alcohol with an alkali metal hydroxide in the presence of the catalyst of the present invention at a temperature between about 100° C. and 220° C., preferably between about 140° C. and about 160° C. At temperatures above about 220° C., the catalyst begins to lose selectivity. At temperatures below about 100° C., satisfactory results can be obtained, but the reaction is slow.

Pressure is required for the reaction to proceed at the temperatures indicated above. However, the reaction pressure is desired to be as low as possible to insure high reaction velocity. Generally, it is necessary to exceed the minimum pressure at which the reaction proceeds in the liquid phase, preferably between about $1.96 \times 10^5$ pascals and about $2.94 \times 10^6$ pascals (about 2 and about 30 kg/cm$^2$), preferably in the range of about is $4.90 \times 10^5$ pascals and about $1.96 \times 10^6$ pascals (about 5 to 20 kg/cm$^2$). The conversion of the alcohol to the corresponding salt of the acid proceeds with the liberation of hydrogen, which should be vented with care from the reaction vessel.

The invention is further illustrated by but not limited to the following examples.

EXAMPLE 1

This comparative example started with only oxidized copper as the catalyst. Diethanolamine (18.86 g, 0.1794 mole), aqueous sodium hydroxide (50 wt %, 30.37 g, 0.380 mole), cupric oxide (3.95 g, 0.0497 mole), and water (28.9 g) were charged to a 0.160 liter nickel autoclave. The reactor was purged with nitrogen and pressurized to 135 psig with nitrogen before heating the mechanically stirred mixture to 160° C. for 12.6 hours while venting gas in excess of 135 psig. This procedure eliminated air in the reactor, which is a source of dissolved oxygen. The oxidized copper content of the reaction mixture was about 38,500 ppm by weight. After filtration of the catalyst, analysis of the product mixture revealed 78.2 mole percent iminodiacetate, 8.8 mole percent hydroxyethylglycine (HEG), a product of incomplete conversion, and 9.7 mole percent glycine by-product based on the initial charge of diethanolamine. The presence of glycine indicates the catalyst is less selective in promoting the desired reaction to form glyphosate. The quantity of glycine is therefore used to evaluate catalyst selectivity, with lower quantities of glycine being evidence of greater catalyst selectivity.

EXAMPLE 2

An essentially identical reaction as described in Example 1, except with reduced metallic copper (Raney copper) in place of cupric oxide, requires 4.2 hours to produce a reaction product that is 93.9 mole percent iminodiacetate, 1.1 mole percent HEG, and 1.6 mole percent glycine. The oxidized copper in the reaction mixture in Example 1 gave six times more glycine than the reaction with reduced copper.

EXAMPLE 3

Diethanolamine (62.71 g, 0.5964 mole), aqueous sodium hydroxide (50 wt %, 101.60 g, 1.270 mole), water (72.5 g), and metallic copper catalyst (Raney copper, 12.84 g, 0.02021 mole) were charged to a 300 ml nickel autoclave equipped with a mechanical stirrer. The vessel was purged with nitrogen and pressurized to 135 psig with nitrogen. This eliminated a source of oxygen. After 2.7 hours of heating at 160° C. all hydrogen evolution had essentially ceased and the reactor was cooled. Analysis of the product mixture after careful filtration of the catalyst to avoid air exposure yielded a iminodiacetate product mixture containing 0.69 mole percent glycine.

EXAMPLE 4

Reuse of the catalyst of Example 3 in a subsequent reaction under conditions essentially identical to those in Example 3 yielded an iminodiacetate product mixture that contained 0.79 mole percent glycine after 3.5 hours.

EXAMPLE 5

Identical reactions to those described in Example 3 above were performed with the exception that the reactor was prepressurized to 100 psig with air instead of nitrogen. Oxygen was not excluded from the reaction mixture. The oxygen concentration in the reaction mixture was about 5 ppm. Analysis of the iminodiacetate product mixtures revealed it contained 0.88 mole percent glycine.

EXAMPLE 6

Identical reactions to those described in Example 4 above were performed with the exception that the reactor was prepressurized to 100 psig with air instead of nitrogen. The oxygen concentration in the reaction mixture was about 5 ppm. Analysis of the iminodiacetate product mixtures revealed it contained 0.94 mole percent glycine.

EXAMPLE 7

Four tests were run to determine the effect of oxidizing agents in the reaction mixture on catalyst selectivity The catalyst was weighed out in water in a tared graduated cylinder. The catalyst was transferred to a 300 ml nickel reactor equipped with a stirrer. For a typical recycle reaction, the nickel vessel was charged with diethanolamine (62.5 grams, 0.59 mole), an aqueous solution of purified-grade NaOH (50 w/w % NaOH, 100 grams, 1.25 mole), a 61.00 grams slurry of recycled Raney copper (Mo promoted, 50 cc, 12.38 grams copper), a 10.29 gram slurry of fresh Raney copper (20 ppm Mo promoted, 10 cc, 0.33 grams copper), an added amount of sodium chlorate to simulate that found in various grades of NaOH, and 12.5 g deionized water. First cycle reaction mixtures were the same as above but with a 61.4 g slurry of fresh purge/replacement catalyst charges. The reactor is sealed and purged three times with nitrogen at 135 psig. The reactor is then pressurized to 135 psig with nitrogen and warmed to 160–170° C. over a period of about 30 minutes. Temperature is maintained at 160° C. until the hydrogen evolution rate drops below detection limit for the mass flow indicator (about 2 cc/min $H_2$). The reaction time is recorded between reaching 160° C. and cessation of the reaction. Stirring is continued until the temperature of the reaction mixture falls below 80° C. For reactions run overnight, the reactor is allowed to cool to ambient temperature with the heating mantle in place and the following day the reaction mixture is warmed to 80–85° C. to facilitate filtration. The catalyst is then separated from the reaction mixture by filtration through a medium glass frit. During filtration, the catalyst is kept covered with a layer of water to prevent oxidation of the catalyst surface. The catalyst cake is washed with sufficient deionized water to remove traces of reaction mixture and the filtrate is collected for an analysis.

Fresh catalyst was recycled in the production of disodium iminodiacetate from diethanolamine. Varying amounts of sodium chlorate were added to the reaction mixture. One molecule of sodium chlorate can generate at least 3 oxidized copper atoms. A minimum estimate of the oxidized copper concentration in the reaction mixture would therefore be about 2800 ppm, 3700 ppm, 7400 ppm, and 0 ppm, respectively. The results listed in Table 1.

TABLE 1

Glycine Production versus Sodium Chlorate Concentration

| NaClO$_3$ Added | NaClO$_3$ in Rx mixture | Glycine (mole %) | Glycolate (mole %) | Formate (mole %) |
| --- | --- | --- | --- | --- |
| 0.39 g | 1,580 ppm | 1.84 | 1.25 | 0.55 |
| 0.51 g | 2,070 ppm | 2.4 | 1.28 | 0.86 |
| 1.02 g | 4,140 ppm | 3.78 | 2.49 | 1.92 |
| 0 g | 0 | 0.96 | 0.25 | 0.02 |

The amounts of glycine byproduct found in the resulting product solutions were found to vary as a function of the amount of sodium chlorate added at the start of each reaction. The reaction yielded about 0.38% glycine, as well as other byproducts, per 1000 ppm of oxidized copper added to the solution by the sodium chlorate.

EXAMPLE 8

A series of tests essentially the same as described in Example 7 were run sequentially to determine the effect of repeated sequential exposure of catalyst to a reaction mixture containing varying amounts of oxidizing reagents. The amount of oxidized copper in the reaction mixture, presuming each molecule of oxidizing agent creates about 3 molecules of oxidized copper, is about 1800 ppm for cycles 2 and 3, about 360 ppm for cycle 6, about 900 ppm for cycle 7, and about 3600 for cycle 8.

The data is presented in Table 2. The reaction yielded about 0.31% glycine, as well as other byproducts, per 1000 ppm of oxidized copper added to the solution by the sodium chlorate.

The amount of selectivity lost due to reuse of catalyst is small relative to the loss of selectivity due to oxidizing reagents. The presence of oxidizing agents appears to have little effect on the long term degradation of catalyst.

TABLE 2

Glycine Production versus Sodium Chlorate Concentration in Sequential Runs

| Cycle | NaClO$_3$ added, g | NaClO$_3$ Rx mixture | Glycine | Corrected* | Glycolate | Formate |
| --- | --- | --- | --- | --- | --- | --- |
| 1 | 0 | 0 | 0.74 | 0.74 | 0.3 | — |
| 2 | 0.25 | 1000 ppm | 1.81 | 1.75 | 1.52 | 0.42 |
| 3 | 0.25 | 1000 ppm | 1.89 | 1.77 | 1.16 | 0.43 |
| 4 | 0 | 0 | 0.94 | 0.76 | 0.48 | 0.27 |
| 5 | 0 | 0 | 0.96 | 0.72 | 0.38 | — |
| 6 | 0.05 | 200 ppm | 1.28 | 0.98 | 0.46 | — |
| 7 | 0.125 | 510 ppm | 1.62 | 1.26 | 0.53 | — |
| 8 | 0.5 | 2030 ppm | 2.4 | 1.98 | 0.83 | 0.52 |
| 9 | 0 | 0 | 1.14 | 0.66 | 0.37 | — |

*corrected glycine concentration for a use related increase of 0.06 mole %/recycle Although the invention has been described in terms of specified embodiments which are set forth in considerable detail, it should be understood that this is by way of illustration only since alternative embodiments and operating techniques will become apparent to those skilled in the art in view of the disclosure. For example, there are numerous methods of reducing oxidized copper in addition to simply excluding gaseous air from the reactor. Accordingly, modifications can be made and other techniques used without departing from the spirit of the described invention.

What is claimed is:

1. A process of manufacturing an amino carboxylic acid salt comprising:
   a) contacting an aqueous solution of a primary aminoalcohol with a strong hydroxide base in the presence of an effective amount of a metallic copper containing catalyst to form a reaction mixture within a reactor; and
   b) reacting the mixture to convert the primary aminoalcohol to an amino carboxylic acid salt, wherein the process further comprises at least one treatment step selected from the group consisting of
   1) pretreating at least one of said aminoalcohol solution, said hydroxide base or said reaction mixture to reduce the content of oxidizing agents therein; and
   2) pretreating said catalyst with an acid to remove oxidized copper therefrom, whereby after said treatment step the reaction mixture contains less than about 3000 ppm of oxidized copper.

2. The process of claim 1 wherein the mixture contains less than about 500 ppm of oxidized copper.

3. The process of claim 1 wherein the mixture contains less than about 100 ppm of oxidized copper.

4. The process of claim 1 wherein the mixture contains less than about 50 ppm of oxidized copper.

5. The process of claim 1 wherein the catalyst comprises a hydroxide-resistant support, an anchor metal deposited on the support, and an element selected from the group consisting of copper, cobalt, nickel, cadmium and mixtures thereof on or combined with the anchor metal.

6. The process of claim 1 wherein the catalyst comprises Raney copper.

7. The process of claim 1 wherein the catalyst comprises Raney copper and also comprises one or more of chromium, titanium, niobium, tantalum, zirconium, vanadium, molybdenum, manganese, tungsten, cobalt, and nickel.

8. The process of claim 1 wherein the concentration of dissolved molecular oxygen in the reactor mixture is less than about 5 ppm.

9. The process of claim 1 wherein the concentration of dissolved molecular oxygen in the reactor mixture is less than about 1 ppm.

10. The process of claim 1 wherein the concentration of dissolved molecular oxygen in the reactor mixture is less than about 0.5 ppm.

11. The process of claim 1 further comprising removing molecular oxygen-containing gas from the reactor.

12. The process of claim 11 wherein air is removed from the reactor by displacement with fluids, by displacement with another gas, by vacuum, or by a combination thereof.

13. The process of claim 1 wherein the reactor mixture comprises between about 5 ppm to about 50 ppm of an oxygen sequestering agent.

14. The process of claim 13 wherein the oxygen sequestering agent is hydrogen sodium sulfite.

15. The process of claim 1 wherein the reactor mixture comprises less than about 1000 ppm of chlorite, chlorate, perchlorate, and hypochlorite salts.

16. The process of claim 1 wherein the mixture comprises less than about 500 ppm of chlorite, chlorate, perchlorate, and hypochlorite salts.

17. The process of claim 1 wherein the mixture comprises less than about 200 ppm of chlorite, chlorate, perchlorate, and hypochlorite salts.

18. The process of claim 1 wherein the mixture comprises less than about 40 ppm of chlorite, chlorate, perchlorate, and hypochlorite salts.

19. The process of claim 1 wherein the strong hydroxide base comprises less than about 500 ppm of chlorite, chlorate, perchlorate, and hypochlorite salts.

20. The process of claim 1 wherein the strong hydroxide base comprises less than about 200 ppm of chlorite, chlorate, perchlorate, and hypochlorite salts.

21. The process of claim 1 wherein the strong hydroxide base comprises less than about 40 ppm of chlorite, chlorate, perchlorate, and hypochlorite salts.

22. The process of claim 1 further comprising exposing the catalyst to acid prior to contacting the catalyst with the strong hydroxide base and primary aminoalcohol.

23. The process of claim 22 wherein the acid comprises organic acid, inorganic acid, EDTA, or mixtures thereof.

24. The process of claim 1 further comprising exposing the catalyst to a reducing agent prior to contacting the catalyst with the strong hydroxide base and primary aminoalcohol.

25. The process of claim 24 wherein the reducing agent comprises one or more of sodium borohydride, formaldehyde, hydrazine, hydrogen, formic acid or salt thereof prior to contacting the catalyst with the strong hydroxide base and primary aminoalcohol.

26. The process of claim 24 wherein the reducing agent comprises formic acid or salt thereof.

27. The process of claim 1 further comprising removing oxidized copper from the aqueous solution comprising the strong hydroxide base with ion exchange resins.

28. The process of claim 1 wherein the aminoalcohol is diethanolamine, the strong hydroxide base is sodium hydroxide, the catalyst comprises Raney copper, and the amino carboxylic acid salt product is disodium iminodiacetate.

29. The process of claim 1 wherein the concentration of oxidized copper in the catalyst prior to reacting the mixture is below about 500 ppm.

30. The process of claim 29 wherein the concentration of oxidized copper in the reaction mixture prior to reacting the mixture is below about 50 ppm.

31. The process of claim 1 wherein the concentration of oxidized copper in the catalyst prior to reacting the mixture is below about 100 ppm.

32. The process of claim 1 wherein the concentration of oxidized copper in the catalyst prior to reacting the mixture is below about 40 ppm.

33. A process for producing an aminocarboxylic acid salt from an aminoalcohol, said process comprising contacting the aminoalcohol with a strong hydroxide base, a copper-containing catalyst, and water, which process is characterized by conducting the reaction while maintaining the oxidized copper concentration in the reaction mixture at 100 ppm or less.

34. The process of claim 28, further comprising the step of converting said disodium iminodiacetate to N-phosphonomethylglycine or a salt thereof.

35. The process of claim 1 wherein said primary aminoalcohol comprises N-phosphonomethylethanolamine or the cyclic internal ester thereof and said amino carboxylic salt comprises a salt of N-phosphonomethylglycine.

36. The process of claim 1 wherein said primary aminoalcohol comprises (N-phosphonomethyl)diethanolamine and said amino carboxylic acid salt comprises a salt of N-phosphonomethyliminodiacetic acid.

37. The process of claim 36, further comprising the step of converting said salt of N-phosphonomethyliminodiacetic acid to N-phosphonomethylglycine or a salt thereof.

38. The process of claim 1 wherein said primary aminoalcohol comprises an $N-(C_{1-6})$ alkyl-N-phosphonomethylethanolamine and said amino carboxylic acid salt comprises a salt of an $N-(C_{1-6})$alkyl-N-phosphonomethyl glycine.

39. The process of claim 38, further comprising the step of converting said $N-(C_{1-6})$alkyl-N-phosphonomethylglycine salt to N-phosphonomethylglycine or a salt thereof.

\* \* \* \* \*